(12) United States Patent
Ashley et al.

(10) Patent No.: US 8,791,096 B2
(45) Date of Patent: Jul. 29, 2014

(54) HEAT STERILIZATION OF GLUCOCORTICOSTEROIDS

(75) Inventors: Adrian Ashley, Cheshire (GB); Paul Lamb, Cheshire (GB); Donald MacDonald, Ayrshire (GB); John Miller, Cheshire (GB); Martin J. Oliver, Cheshire (GB); Mathew Pollard, Cheshire (GB)

(73) Assignee: Norton Healthcare Ltd, London (GB)

( * ) Notice: Subject to any disclaimer, the term of this patent is extended or adjusted under 35 U.S.C. 154(b) by 1528 days.

(21) Appl. No.: 10/594,861

(22) PCT Filed: May 17, 2005

(86) PCT No.: PCT/US2005/017292
§ 371 (c)(1),
(2), (4) Date: Dec. 5, 2007

(87) PCT Pub. No.: WO2005/115332
PCT Pub. Date: Dec. 8, 2005

(65) Prior Publication Data
US 2008/0139519 A1    Jun. 12, 2008

(30) Foreign Application Priority Data
May 17, 2004 (GB) .................. 0410995.5

(51) Int. Cl.
*A61K 31/56* (2006.01)
*A61L 2/00* (2006.01)
*C07J 5/00* (2006.01)

(52) U.S. Cl.
CPC ............. *A61L 2/0023* (2013.01); *A61L 2/0011* (2013.01); *A61K 31/56* (2013.01); *C07J 5/00* (2013.01)
USPC ...................................................... 514/179

(58) Field of Classification Search
CPC .............................. A61L 2/0023; C07J 5/00
USPC ............................................................ 514/179
See application file for complete search history.

(56) References Cited

U.S. PATENT DOCUMENTS

| | | | |
|---|---|---|---|
| 3,962,430 A | 6/1976 | O'Neill | |
| 5,993,781 A | 11/1999 | Snell et al. | |
| 6,066,292 A * | 5/2000 | Purwar | 422/1 |
| 6,392,036 B1 * | 5/2002 | Karlsson et al. | 540/63 |
| 6,464,958 B1 | 10/2002 | Bernini et al. | |
| 2002/0065256 A1 | 5/2002 | Karlsson et al. | |
| 2003/0103864 A1 * | 6/2003 | McAffer et al. | 422/1 |
| 2006/0140816 A1 * | 6/2006 | Gentile et al. | 422/26 |

FOREIGN PATENT DOCUMENTS

| | | | | |
|---|---|---|---|---|
| DE | 10145361 A1 | | 3/2003 | |
| EP | 1454636 | * | 9/2004 | ............. A61L 2/07 |
| WO | WO-9531964 | | 11/1995 | |
| WO | WO-99/32156 A2 | | 7/1999 | |
| WO | WO-99/36055 A1 | | 7/1999 | |
| WO | WO-0025746 A2 | | 5/2000 | |
| WO | 02/41925 | | 5/2002 | |

OTHER PUBLICATIONS

Illum et al., Arch. Pharm. Chemi Sci. Ed. 2, 2(6); 167-174 (1974).
Notification of the Second Office Action, Chinese Patent Application No. 201210068425.7, Apr. 15, 2014, English Translation Included, 21 pp.

* cited by examiner

*Primary Examiner* — Paul Zarek
(74) *Attorney, Agent, or Firm* — RatnerPrestia

(57) ABSTRACT

The present invention provides a method for the sterilization of a labile glucocorticosteroid, which method comprises heat-treating by moist heat the labile glucocorticosteroid in the form of a suspension for a sterilizing-effective time. The methods and compositions according to the invention are useful as therapeutic tools to prevent, reverse, and/or reduce the symptoms of allergic and/or inflammatory conditions in a mammalian patient. The invention also provides methods and compositions, which may be manipulated and fine-tuned to fit the condition(s) to be treated while producing fewer side effects.

11 Claims, 4 Drawing Sheets

HEAT STERILIZATION OF GLUCOCORTICOSTEROIDS

CROSS REFERENCE TO RELATED APPLICATIONS

The present application is a national phase entry under 35 U.S.C. §371 of International Application No. PCMS2005/017292, filed May 17, 2005, published in English, which claims priority of United Kingdom Patent Application No. 0410995.5, filed May 17, 2004. The disclosures of all of said applications are incorporated by reference herein.

TECHNICAL FIELD OF THE INVENTION

The present invention relates to methods for the heat sterilization of a suspension form of a labile glucocorticosteroid, sterile pharmaceutical compositions, and methods for the treatment of allergic and/or inflammatory conditions using the same.

BACKGROUND OF THE INVENTION

Sterile drug products provide a number of benefits, both medically and economically. The medical ramifications requiring sterile drug preparations are obvious in that the use of non-sterile preparations may subject the patient to an unnecessary risk of secondary infection from the contaminating microbe, a microbe that is at least resistant to the drugs of the preparation. Furthermore, even if the contaminant is innocuous, the growth can result in loss of active drug products per se with possible concomitant generation of toxic by-products. Economically, contaminated drug products have a shortened shelf life, which requires increased production expenses to replace product on a more frequent basis.

Methods are needed for the preparation of sterile products for patient use. However, the problem associated with many sterilization procedures is that the process often results in unfavorable changes in the drug profile. These changes in the drug profile can range from loss of activity, to increased degradation products being created, or possible alteration of the chemical or physical characteristics of the compound sterilized. These problems are especially pronounced when glucocorticosteroids are sterilized.

Sterilization of materials relies on the input of sufficient energy to be lethal to any potential microbial contamination. Numerous methods including heat, radiation, and chemicals have been proposed for the sterilization of glucocorticosteroids. However, to date these methods often result in the excess production of degradants or a loss of activity for the glucocorticosteroid being sterilized. Additionally, as in the case of glucocorticosteroid suspension formulations for metered dose inhalation, the commonly used sterilization procedures often results in unacceptable changes to drug particle size.

Chemical sterilization, for the most part, has been based on exposure to toxic compounds, for example, ethylene oxide. However, when used to sterilize glucocorticosteroids, ethylene oxide has been found to leave residual amounts of ethylene oxide in the drug preparation. Ethylene oxide is toxic and the residual levels are often above the pharmaceutically acceptable limits as set by most regulatory agencies.

Irradiation based sterilization is known and has been recommended for glucocorticosteroids (see Illum and Moeller in *Arch. Pharm. Chemi. Sci.*, Ed. 2, 1974, pp. 167-174). However, significant degradation has been reported when irradiation has been used to sterilize micronized glucocorticosteroids.

WO 02/41925 to Breath Limited purportedly discloses a rapid method, similar to pasteurization, for the sterilization of compositions. This method entails pumping the composition to be sterilized through stainless steel pipes and rapidly raising the temperature of the composition to about 130-145° C. for about 2-20 seconds, subsequently followed by rapid cooling in seconds to ambient conditions.

U.S. Pat. No. 3,962,430 to O'Neil discloses a method for the production of sterile isotonic solutions of medicinal agents. The method comprises adding the medicinal agent to a saturated solution of sodium chloride in water at 100° C. The drug/saturated sodium chloride solution is then heated to 100-130° C. This method, which purportedly is based on the theory that the sodium chloride ions tie up free water, thereby preventing hydrolytic degradation, is not suitable for suspensions of fine particles of glucocorticosteroids intended for inhalation, as the procedure produces unfavorable changes in the size of the particles. Additionally, the procedure can result in bridge formation between drug particles producing large aggregates, which do not break up on administration.

U.S. Pat. No. 6,464,958 to Bernini, et al., discloses that heat sterilization of suspension formulations for many drugs produces unfavorable changes in the drug profile including, for example, aggregation of drug particles. Some of the unfavorable changes are correctable. For example, aggregates formed during heat sterilization could be re-treated to brake up the aggregates into smaller sized particles suitable for nasal administration. However, some unfavorable changes cannot be corrected, as in the case of beclomethasone dipropionate. For example, Bernini reports that beclomethasone suspensions sterilized by a wet steam process similar to that reported in U.S. Pat. No. 3,962,430 supra, undergo a marked decrease in active ingredient content (about 8-9%), with a concomitant increase in degradation products (about 10-11%).

Karlsson, et al., in U.S. Pat. No. 6,392,036 discloses a method for the dry heat sterilization of powdered glucocorticosteroids that can then be used for drug formulations.

Methods are needed to sterilize suspension glucocorticosteroid pharmaceutical compositions. Sterilization should occur without producing pharmaceutically unacceptable changes to drug particle size while concomitantly minimizing degradation product production and loss of drug activity. Ideally, for sterile pharmaceutical products, the last stage of preparation of the product should be the sterilization process, thereby minimizing the potential for contamination during manufacture.

SUMMARY OF THE INVENTION

The present invention provides a method for the sterilization of a glucocorticosteroid, comprising the step of heating an aqueous suspension of a glucocorticosteroid, wherein the glucocorticosteroid has a sufficiently low solubility in water and is used in a sufficient amount that at least 50% of the glucocorticosteroid is in the form of a suspension during heating.

An aspect of the invention discloses a method for the sterilization of a labile glucocorticosteroid, comprising the step of exposing to moist heat a suspension of a labile glucocorticosteroid for a sterilizing-effective time.

Another aspect of the invention discloses compositions comprising a sterile labile glucocorticosteroid suspension prepared according to the methods disclosed herein.

The ordinate identifies the concentrates tested while the abscissa indicates the budesonide content present (as a percentage).

Figure 2:
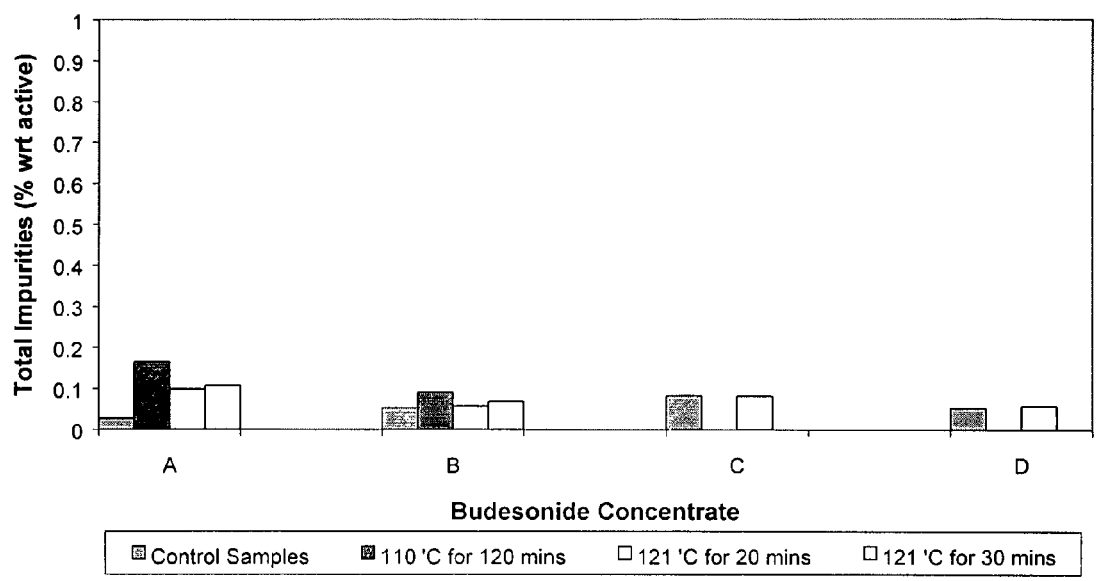

FIG. 2: Graphic representation of total budesonide impurities (both known and unknown) in concentrated samples following sterilization. The ordinate identifies the concentrates tested while the abscissa indicates the percentage of impurities present following heating.

Figure 3:
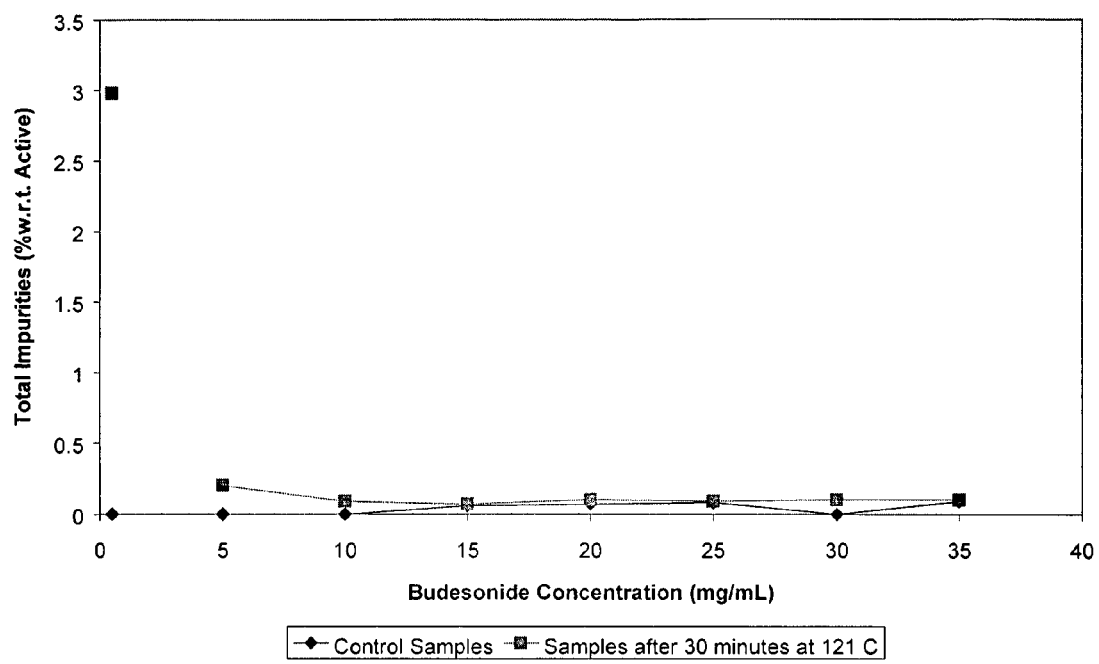

FIG. 3: Graphic representation of budesonide degradants in diluted samples following sterilization. The ordinate identifies the budesonide concentration (mg/ml) tested, whereas the abscissa indicates the impurity levels present following heating.

Figure 4:
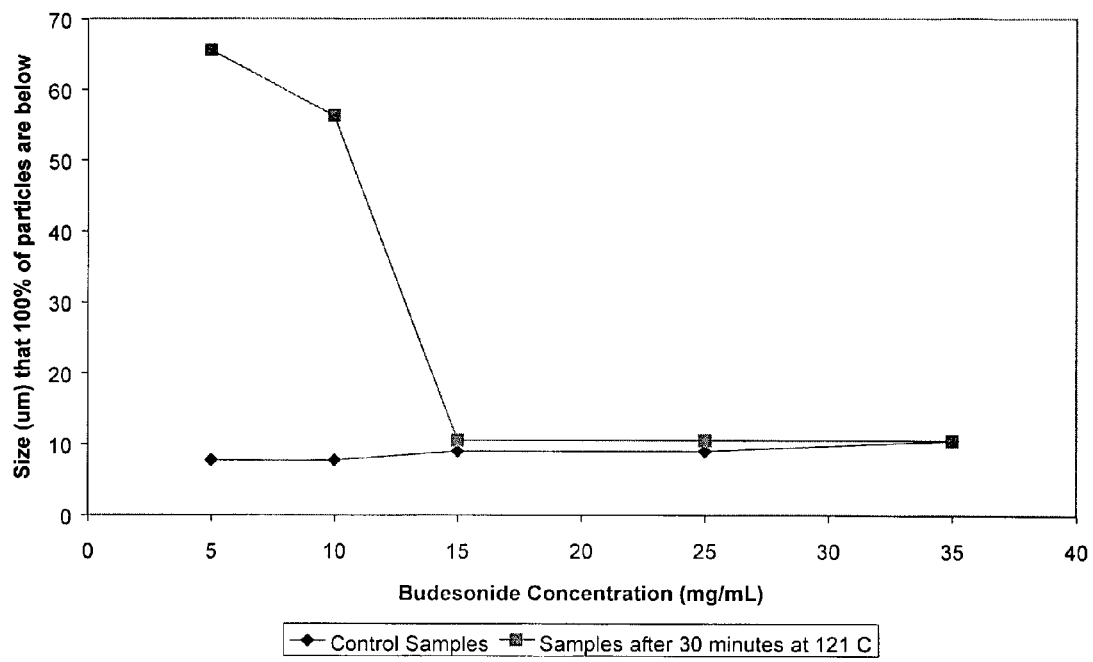

FIG. 4: Graphic representation of maximum budesonide particle size distribution in diluted samples following sterilization. The ordinate identifies the budesonide concentration (mg/ml) tested, whereas the abscissa indicates the upper threshold for particle size following heating of the suspension formulation.

DETAILED DESCRIPTION OF THE INVENTION

The present invention provides a method for the sterilization of a glucocorticosteroid, comprising the step of heating an aqueous suspension of a glucocorticosteroid, wherein the glucocorticosteroid has a sufficiently low solubility in water and is used in a sufficient amount that at least 50% of the glucocorticosteroid is in the form of a suspension during heating. The methods and compositions according to the invention are useful as therapeutic tools to prevent, reverse, and/or reduce the symptoms of allergic and/or inflammatory conditions in a mammalian patient. The invention also provides methods and compositions using the same, which may be manipulated and fine-tuned to fit the condition(s) to be treated while producing fewer side effects.

The glucocorticosteroid is preferably "labile" meaning the state of chemical or physical instability brought about by external forces applied to the chemical compound or composition. By way of non-limiting example, acid labile or temperature labile would mean that the chemical compound undergoes unacceptable degradation (e.g., pharmaceutical or physicochemical) when exposed respectively to specific acidic or temperature conditions.

As used herein, "glucocorticosteroid" or "glucocorticoid" refers to any of a group of steroid hormones (including derivatives, synthetic analogs, and pro-drugs), such as cortisone, which are produced by the adrenal cortex. These compounds are involved in carbohydrate, protein, and fat metabolism. Additionally, the glucocorticosteroids may have anti-inflammatory properties.

The glucocorticosteroids used in the invention are preferably anti-inflammatory glucocorticosteroids. Non-limiting examples of glucocorticosteroids, which may be used in the present invention, include beclomethasone, budesonide, ciclesonide, cortivazol, deflazacort, flumethasone, flunisolide, fluocinolone, fluticasone, mometasone, rofleponide, tipredane and triamcinolone. Preferably, use is made of budesonide, beclomethasone (e.g. the dipropionate), ciclesonide, fluticasone, mometasone and triamcinolone. Most preferably, use is made of budesonide and beclomethasone.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention.

The patent and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

In the specification and the appended claims, singular forms, including the singular forms "a," "an" and "the", specifically also encompass the plural referents of the terms to which they refer unless the context clearly dictates otherwise. In addition, as used herein, unless specifically indicated otherwise, the word "or" is used in the "inclusive" sense of "and/or" and not the "exclusive" sense of "either/or."

As used in this specification, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention An aspect of the invention provides a method for the heat sterilization of a labile glucocorticosteroid. The method of this aspect comprises the step of exposing to moist heat a suspension of a labile glucocorticosteroid for a sterilizing-effective time. The applicant has found that an undesirable increase in the particle size of the glucocorticosteroid as well as the formation of unwanted by-products may be avoided by careful restriction of the sterilization parameters and the nature of the glucocorticosteroid. The glucocorticosteroid must have a sufficiently low solubility in the suspending solvent and be employed in a sufficiently high concentration that only a minor portion of the glucocorticosteroid dissolves in the suspending solvent. In this manner, degradation of the glucocorticosteroid results in minimal by-products and recrystallisation of the glucocorticosteroid on cooling leading to an undesirable increase in particle size may be avoided.

A balance is required between the Solubility of the glucocorticosteroid and the amount of the glucocorticosteroid used per unit of solvent such that at least 50% of the glucocorticosteroid is suspended in the solvent. For example, for budesonide, at the sterilizing temperatures used herein the water solubility is about 7 mg/ml. Therefore, using 15 mg of budesonide per 1 mg water provides 53% of budesonide as a suspension. Preferably at least 60% of the glucocorticosteroid is suspended in the solvent although this value could be at least 70% or at least 80%.

In this manner, it is unnecessary to incorporate additional components to regulate the solubility of the glucocorticosteroid in water, for example sodium chloride in amount sufficient to form a saturated solution of sodium chloride as set out in U.S. Pat. No. 3,962,430 (described above). Preferably the method of the present invention is carried out with substantially no solubility regulators present, that is no components which have a significant effect on the solubility of the glucocorticosteroid in water.

The maximum amount of the glucocorticosteroid is less important provided a suspension is still formed. An excess of glucocorticosteroid would otherwise form a paste which is difficult to handle. By way of an example, the maximum preferred amount of budesonide is about 150 mg/ml.

Heating the suspension under these conditions prevents an undesirable increase in impurities as may be seen in the examples presented hereinbelow. For example, for budesonide, it is preferred that the level of the degradation product 1,2-dihydro budesonide be less than 0.2% by weight based on the amount of budesonide present in the suspension. The degradation products may be measured by standard techniques, such as by HPLC as described in the examples hereinbelow.

In an embodiment, the labile glucocorticosteroid is budesonide, and the step of heating is by autoclaving at about 121° C. for about 20 to about 30 minutes or at about 110° C. for about 115 to about 150 minutes. Another embodiment contemplates that the labile glucocorticosteroid is beclomethasone dipropionate, and the step of heating is by autoclaving at about 121° C. for about 20 to about 30 minutes or at about 110° C. for about 115 to about 150 minutes. The labile glucocorticosteroid in yet other embodiments is at a concentration of from about 15 mg/ml to about 150 mg/ml.

As used herein, "moist heat," means the application to a composition of heat to effect sterilization of the composition being treated by the transfer of heat to the water resulting in the partial vaporization of a water to form steam when heated above 100° C. The moist heat may apply heat to the compound or composition in the range of from about 101 to about 145° C., preferably from about 110 to about 138° C., and most preferably from about 121 to about 138° C. Preferably, heating is by autoclaving.

To be "sterile" means that a product or composition meets the criteria of sterility according to the US Pharmacopoeia 27/NF22, 2004, or its counterpart in other jurisdictions, and which provides a therapeutically acceptable glucocorticosteroid and/or pharmaceutical formulation.

The term "sterilizing-effective time" means the minimal amount of time required to effect sterilization under the specific conditions specified. Preferably the sterilizing-effective time is from about 2 minutes to about 180 minutes.

In another embodiment, the glucocorticosteroid suspension further comprises a pharmaceutically acceptable surfactant which are well known in the art, such as Polysorbates, e.g. Polysorbate 80. When present, the surfactant is preferably at a concentration of from about 0.2 mg/ml to about 60 mg/ml.

Other embodiments of this aspect of the invention further comprise the step of diluting the suspension to a pharmaceutically suitable concentration with pharmaceutically acceptable excipients, diluents, etc.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable, which is inherently continuous, the variable can be equal to any real value of the numerical range, including the end-points. As an example, a variable which is described as having values between 0 and 2, can be 0, 1 or 2 for variables which are inherently discrete, and can be 0.0, 0.1, 0.01, 0.001, or any other real value for variables which are inherently continuous.

The methods and compositions of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammal in need" include humans as well as non-human mammals, particularly domesticated animals including, without limitation, cats, dogs, and horses.

Another aspect of the invention provides suspension compositions of sterilized labile glucocorticosteroids prepared according to the methods of the first aspect of the invention described above. In some embodiments, the composition is a pharmaceutical composition for treating or alleviating the symptoms of allergic and/or inflammatory conditions in a mammalian patient. In these embodiments, the compositions comprise a therapeutically effective amount of sterilized, labile glucocorticosteroid(s) in a pharmaceutically acceptable vehicle. In some embodiments, the glucocorticosteroid is budesonide while in yet other embodiments beclomethasone is used.

The term "therapeutically effective amount" is used to denote treatments at dosages effective to achieve the therapeutic result sought. Furthermore, one of skill will appreciate that the therapeutically effective amount of the compound of the invention may be lowered or increased by fine tuning and/or by administering more than one compound of the invention, or by administering a compound of the invention with another compound. The invention therefore provides a method to tailor the administration/treatment to the particular exigencies specific to a given mammal.

Other embodiments contemplate compositions presenting the labile glucocorticosteroid in combination with a second active ingredient. In some embodiments, the second active ingredient may be selected from albuterol, ipratropium bromide and cromolyn.

In yet other embodiments of this aspect, the compositions of the invention are formulated to be suitable for oral, inhalation, rectal, ophthalmic (including intravitreal or intracameral), nasal, topical (including buccal and sublingual), vaginal, or parenteral (including subcutaneous, intramuscular, intravenous, intradermal, and intratracheal) administration. Preferably the composition is formulated for inhalation in which case the particle size of the glucocorticosteroid is preferably such that the Dv100 is less than 20 μm, the Dv90 is less than 10 μm and the Dv50 is less than 5 μm, where Dvn represents the volume diameter at the nth percentile. The volume diameter is a known term in the art and indicates the diameter that a sphere would have when it has the volume of the particle. The particle sizes may be measured by standard techniques, such as by laser diffraction as described in the examples hereinbelow. Such a particle sizes may be achieved using the heat sterilisation conditions as described herein.

The formulations of the compositions of the invention may conveniently be presented in unit dosage form and may be prepared by conventional pharmaceutical techniques. Such techniques include the step of bringing into association the compounds of the invention and the pharmaceutically acceptable carrier(s), such as a diluent or an excipient. In general, the compositions are prepared by uniformly and intimately bringing into association the active ingredient with liquid or finely divided solid carriers or both, and then, if necessary, shaping the product.

The sterile labile glucocorticosteroids prepared according to the invention are optionally formulated in a pharmaceutically acceptable vehicle with any of the well known pharmaceutically acceptable carriers, including diluents and excipients (see *Remington's Pharmaceutical Sciences*, 18th Ed., Gennaro, Mack Publishing Co., Easton, Pa. 1990 and *Remington: The Science and Practice of Pharmacy*, Lippincott, Williams & Wilkins, 1995). The type of pharmaceutically acceptable carrier/vehicle employed in generating the compositions of this aspect of the invention will vary depending upon the mode of administration of the composition to the mammal. Generally, pharmaceutically acceptable carriers are physiologically inert and nontoxic. Formulations of compositions according to the invention may contain more than one type of pharmacologically active ingredient useful for the treatment of the symptom/condition being treated.

In yet another aspect, the invention provides methods for using compositions of the invention for treating or alleviating the symptoms of allergic and/or inflammatory conditions in a mammalian patient. Such methods comprise the administration of a therapeutically effective amount of the labile glucocorticosteroid in a pharmaceutically acceptable vehicle. In various embodiments of this aspect, administration of a therapeutically effective amount of the glucocorticosteroid, either alone or in combination with a second active agent, is by oral, inhalation, rectal, ophthalmic, vaginal, or parenteral administration. In some embodiments, the glucocorticosteroid is budesonide while in yet other embodiments the glucocorticosteroid is beclomethasone.

The invention further provides a sterile glucocorticosteroid, preferably an anti-inflammatory glucocorticosteroid, for use in the treatment of allergic and/or inflammatory conditions. The allergic and/or inflammatory conditions to be treated need not be confined to one anatomic site, for example, the nose or lungs, and the compositions of the invention are formulated for administration appropriate to the site of treatment. Allergic and/or inflammatory conditions include, without limitation, contact dermatitis, asthma, rhinitis, or chronic obstructive pulmonary disease. The invention also provides for the use of sterile glucocorticosteroid compositions, in the manufacture of a medicament (preferably a sterile medicament) for use in the treatment of allergic and/or inflammatory conditions.

The following examples are intended to further illustrate certain embodiments of the invention and are not limiting in nature. Those skilled in the art will recognize, or be able to ascertain, using no more than routine experimentation, numerous equivalents to the specific substances and procedures described herein.

EXAMPLES

Example 1

Heat Sterilization of Budesonide

Concentrated budesonide samples were prepared by dispersing the solid material by homogenization using a high shear mixer, placing in a sealed container and subjected to heating for the times and at the temperatures indicated in Table 1. The samples were heated for the times and temperatures indicated.

The heated, concentrated samples were subsequently analyzed to determine budesonide content and impurity levels (both known and unknown) by HPLC analysis with a UV/vis detector, the results of which are presented in Tables 2-5.

Figure 1:
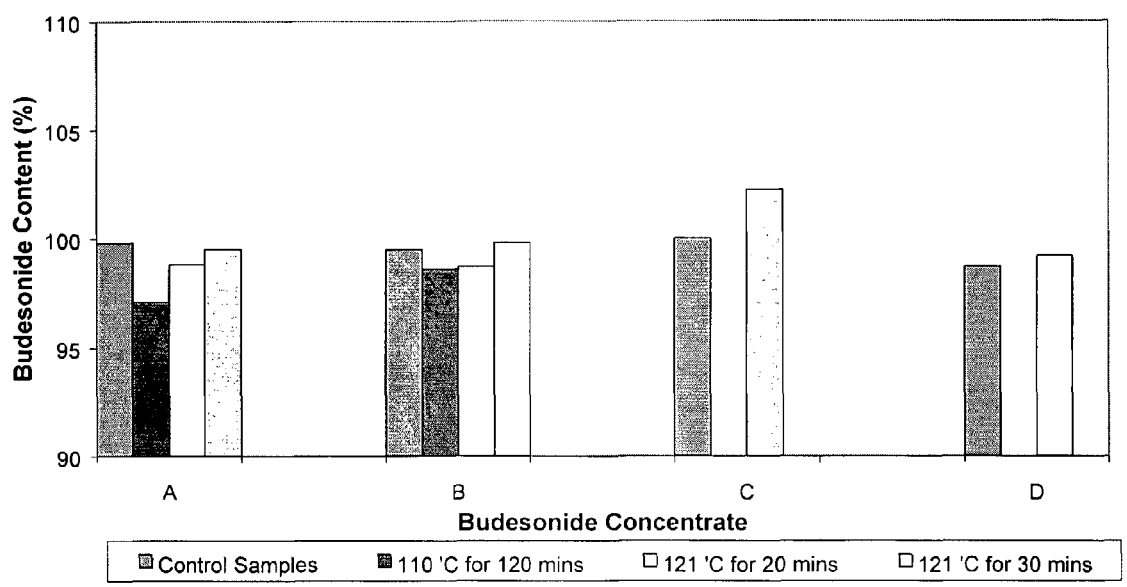
FIG. 1: Graphic representation of the budesonide content in concentrated budesonide samples following sterilization.

The concentrated budesonide samples were also subjected to particle size analysis by Laser Diffraction, the distribution of which is presented in Table 6. FIGS. 1 and 2 graphically display respectively the budesonide content and total impurities of the heat stressed concentrates.

Sterilization was confirmed by use of spore strip bioindicators which were treated concomitantly with the sample concentrates.

The results show that the treatment (121° C. for 20 minutes) of the higher concentrations tested (concentrates B, C, & D) tended to show the least amount of heat induced degradation (0.004, 0 and 0.003% difference from untreated controls respectively, Tables 3-5). The heat induced degradation, while acceptable, was greatest for concentrate A (37.5 mg/ml). Comparable results were also observed for the particle size analysis presented in Table 6.

TABLE 1

Formulations of Budesonide Concentrates and Final Budesonide Aqueous Suspension Product

| | | Budesonide Concentration (mg/ml) | Heating Regimen (° C./minutes) |
|---|---|---|---|
| Budesonide | Concentrate A | 37.5 | 110/120 |
| | | | 121/20 |
| | | | 121/30 |
| | Concentrate B | 75 | 110/120 |
| | | | 121/20 |
| | | | 121/30 |
| | Concentrate C | 75 | 121/20 |
| | Concentrate D | 150 | 121/20 |
| | Final Product | 0.5 | |
| Polysorbate 80 Ph. Eur. | Concentrate A | 0.75 | |
| | Concentrate B | 1.5 | |
| | Concentrate C | 30 | |
| | Concentrate D | 60 | |
| | Final Product | 0.2 | |
| Sodium Chloride Ph. Eur. | All | 8.5 | |
| Sodium Citrate Dihydrate Ph. Eur. | All | 0.5 | |
| Citric Acid Monohydrate Ph. Eur. | All | 0.31 | |
| Disodium Edetate Dihydrate Ph. Eur. | All | 0.1 | |

TABLE 2

Budesonide Content and Related Substances Results for Heated Budesonide Concentrates

| CONCENTRATE A | Control | | 110° C. for 120 minutes | | 121° C. for 20 minutes | | 121° C. for 30 minutes | |
|---|---|---|---|---|---|---|---|---|
| Budesonide Content (%) | 99.8 | 99.7 | 96.6 | 97.6 | 98.7 | 98.9 | 99.9 | 99.0 |
| Total Budesonide Content (%) | 99.8 | | 97.1 | | 98.8 | | 99.5 | |
| | | | Impurities (% wrt active) | | | | | |
| Desonide | ND | ND | ND | ND | ND | ND | ND | ND |
| 16α-hydroxypredinisolone | 0.027 | 0.030 | 0.024 | 0.021 | 0.048 | 0.043 | 0.031 | 0.035 |
| 21-dehydro-budesonide | 0.054 | 0.046 | 0.119 | 0.083 | 0.065 | 0.074 | 0.077 | 0.072 |
| Budesonide 1,2 dihydro | 0.017 | 0.018 | 0.021 | 0.020 | 0.019 | 0.020 | 0.020 | 0.021 |
| 22-Methyl homologue | ND | ND | 0.016 | 0.016 | 0.026 | 0.022 | ND | ND |
| D-homobudesonide | 0.022 | 0.022 | 0.020 | 0.019 | 0.021 | 0.020 | 0.021 | 0.021 |
| 14,15-dehydrobudesonide | ND | ND | ND | ND | ND | ND | ND | ND |
| S-11-Keto budesonide | 0.017 | 0.022 | 0.030 | 0.032 | 0.025 | 0.023 | 0.025 | 0.025 |
| R-11-Keto budesonide | 0.022 | 0.023 | 0.032 | 0.036 | 0.031 | 0.030 | 0.030 | 0.031 |
| S-21-Acetate budesonide | ND | ND | ND | ND | ND | ND | ND | ND |
| R-21-Acetate budesonide | ND | ND | ND | ND | ND | ND | ND | ND |
| Total Knowns | 0.054 | 0.000 | 0.119 | 0.083 | 0.065 | 0.074 | 0.077 | 0.072 |
| Average Total Knowns | 0.027 | | 0.101 | | 0.070 | | 0.075 | |
| Max Unknown | 0.031 | 0.032 | 0.062 | 0.065 | 0.016 | 0.057 | 0.034 | 0.064 |
| Total Unknowns | 0.000 | 0.000 | 0.062 | 0.065 | 0.000 | 0.057 | 0.000 | 0.064 |
| Average Total Unknowns | 0.000 | | 0.064 | | 0.029 | | 0.032 | |
| Total Impurities | 0.054 | 0.000 | 0.181 | 0.148 | 0.065 | 0.131 | 0.077 | 0.136 |
| Average Total Impurities | 0.027 | | 0.164 | | 0.098 | | 0.107 | |

Note:
only impurities at levels greater than 0.05% wrt active have been used to calculate the totals since levels below 0.05% wrt active cannot be accurately quantified.
ND—not detectable (i.e. below the limit of detection)

TABLE 3

Budesonide Content and Related Substances Results for Heated Budesonide Concentrate B

| CONCENTRATE B | Control | | 110° C. for 120 minutes | | 121° C. for 20 minutes | | 121° C. for 30 minutes | |
|---|---|---|---|---|---|---|---|---|
| Budesonide Content (%) | 99.8 | 99.1 | 98.6 | 98.6 | 99.0 | 98.3 | 99.9 | 99.7 |
| Total Budesonide Content (%) | 99.5 | | 98.6 | | 98.7 | | 99.8 | |
| | | | Impurities (% wrt active) | | | | | |
| Desonide | ND | ND | ND | ND | ND | ND | ND | ND |
| 16α-hydroxypredinisolone | 0.039 | 0.039 | 0.055 | 0.048 | 0.058 | 0.056 | 0.040 | 0.045 |
| 21-dehydro-budesonide | 0.026 | 0.026 | 0.042 | 0.060 | 0.025 | 0.029 | 0.070 | 0.065 |
| Budesonide 1,2 dihydro | 0.017 | 0.019 | 0.021 | 0.021 | 0.019 | 0.019 | 0.019 | 0.018 |
| 22-Methyl homologue | 0.023 | 0.024 | 0.042 | 0.034 | 0.043 | 0.037 | 0.019 | 0.026 |
| D-homobudesonide | 0.021 | 0.021 | 0.020 | 0.020 | 0.020 | 0.020 | 0.020 | 0.020 |
| 14,15-dehydrobudesonide | ND | ND | ND | ND | ND | ND | ND | ND |
| S-11-Keto budesonide | 0.023 | 0.025 | 0.034 | 0.030 | 0.019 | 0.018 | 0.018 | 0.020 |
| R-11-Keto budesonide | 0.029 | 0.029 | 0.033 | 0.035 | 0.043 | 0.024 | 0.024 | 0.024 |
| S-21-Acetate budesonide | ND | ND | ND | ND | ND | ND | ND | ND |
| R-21-Acetate budesonide | ND | ND | ND | ND | ND | ND | ND | ND |
| Total Knowns | 0.000 | 0.000 | 0.055 | 0.060 | 0.058 | 0.056 | 0.070 | 0.065 |
| Average Total Knowns | 0.000 | | 0.058 | | 0.057 | | 0.068 | |
| Max Unknown | 0.031 | 0.051 | 0.067 | 0.044 | 0.029 | 0.029 | 0.029 | 0.047 |
| Total Unknowns | 0.000 | 0.051 | 0.067 | 0.000 | 0.000 | 0.000 | 0.000 | 0.000 |
| Average Total Unknowns | 0.026 | | 0.034 | | 0.000 | | 0.000 | |
| Total Impurities | 0.000 | 0.051 | 0.122 | 0.060 | 0.058 | 0.056 | 0.070 | 0.065 |
| Average Total Impurities | 0.026 | | 0.091 | | 0.057 | | 0.068 | |

Note:
only impurities at levels greater than 0.05% wrt active have been used to calculate the totals since levels below 0.05% wrt active cannot be accurately quantified.
ND—not detectable (i.e. below the limit of detection)

TABLE 4

Budesonide Content and Related Substances Results for Heated Budesonide Concentrate C

| CONCENTRATE C | Control | | 121° C. for 20 minutes | |
|---|---|---|---|---|
| Budesonide Content (%) | 100.2 | 99.8 | 102.3 | 102.0 |
| Total Budesonide Content (%) | 100.0 | | 102.2 | |
| Impurities (% wrt active) | | | | |
| Desonide | ND | ND | ND | ND |
| 16α-hydroxypredinisolone | 0.044 | 0.053 | 0.054 | 0.046 |
| 21-dehydro-budesonide | 0.025 | 0.022 | 0.027 | 0.051 |
| Budesonide 1,2 dihydro | 0.020 | 0.020 | 0.022 | 0.023 |
| 22-Methyl homologue | 0.027 | 0.039 | 0.040 | 0.035 |
| D-homobudesonide | 0.021 | 0.021 | 0.020 | 0.020 |
| 14,15-dehydrobudesonide | ND | ND | ND | ND |
| S-11-Keto budesonide | 0.023 | 0.025 | 0.027 | 0.031 |
| R-11-Keto budesonide | 0.027 | 0.028 | 0.030 | 0.036 |
| S-21-Acetate budesonide | ND | ND | ND | ND |
| R-21-Acetate budesonide | ND | ND | ND | ND |
| Total Knowns | 0.000 | 0.053 | 0.054 | 0.051 |
| Average Total Knowns | 0.027 | | 0.053 | |
| Max Unknown | 0.055 | 0.056 | 0.040 | 0.056 |
| Total Unknowns | 0.055 | 0.056 | 0.000 | 0.056 |
| Average Total Unknowns | 0.056 | | 0.028 | |
| Total Impurities | 0.055 | 0.109 | 0.054 | 0.107 |
| Average Total Impurities | 0.082 | | 0.081 | |

Note:
only impurities at levels greater than 0.05% wrt active have been used to calculate the totals since levels below 0.05% wrt active cannot be accurately quantified.
ND—not detectable (i.e. below the limit of detection)

TABLE 5

Budesonide Content and Related Substances Results for Heated Budesonide Concentrate D

| CONCENTRATE D | Control | | 121° C. for 20 minutes | |
|---|---|---|---|---|
| Budesonide Content (%) | 98.6 | 98.7 | 98.9 | 99.4 |
| Total Budesonide Content (%) | 98.7 | | 99.2 | |
| Impurities (% wrt active) | | | | |
| Desonide | ND | ND | ND | ND |
| 16α-hydroxypredinisolone | 0.047 | 0.048 | 0.059 | 0.055 |
| 21-dehydro-budesonide | 0.025 | 0.031 | 0.028 | 0.034 |
| Budesonide 1,2 dihydro | 0.022 | 0.024 | 0.025 | 0.029 |
| 22-Methyl homologue | 0.031 | 0.031 | 0.047 | 0.040 |
| D-homobudesonide | 0.021 | 0.021 | 0.020 | 0.020 |
| 14,15-dehydrobudesonide | ND | ND | ND | ND |
| S-11-Keto budesonide | 0.021 | 0.023 | 0.023 | 0.023 |
| R-11-Keto budesonide | 0.026 | 0.030 | 0.030 | 0.032 |
| S-21-Acetate budesonide | ND | ND | ND | ND |
| R-21-Acetate budesonide | ND | ND | ND | ND |
| Total Knowns | 0.000 | 0.000 | 0.059 | 0.055 |
| Average Total Knowns | 0.000 | | 0.057 | |
| Max Unknown | 0.052 | 0.051 | 0.042 | 0.045 |
| Total Unknowns | 0.052 | 0.051 | 0.000 | 0.000 |
| Average Total Unknowns | 0.052 | | 0.000 | |
| Total Impurities | 0.052 | 0.051 | 0.059 | 0.055 |
| Average Total Impurities | 0.052 | | 0.057 | |

Note:
only impurities at levels greater than 0.05% wrt active have been used to calculate the totals since levels below 0.05% wrt active cannot be accurately quantified.
ND—not detectable (i.e. below the limit of detection)

TABLE 6

Particle Size Distribution Results for Heated Budesonide Concentrates

| | | Average Values in μm | | | | |
|---|---|---|---|---|---|---|
| Concentrate | Heating Regime | Dv10* | Dv50* | Dv90* | SPAN** | D[4, 3]† |
| A | Control | 0.46 | 1.48 | 3.04 | 1.75 | 1.64 |
| | 110° C. for 120 mins (1) | 0.50 | 1.72 | 3.52 | 1.76 | 1.89 |
| | 110° C. for 120 mins (2) | 0.48 | 1.73 | 3.62 | 1.81 | 1.91 |
| | 121° C. for 20 mins (1) | 0.49 | 1.73 | 3.57 | 1.78 | 1.90 |
| | 121° C. for 20 mins (2) | 0.49 | 1.73 | 3.60 | 1.80 | 1.91 |
| | 121° C. for 30 mins (1) | 0.50 | 1.72 | 3.54 | 1.76 | 1.90 |
| | 121° C. for 30 mins (2) | 0.49 | 1.74 | 3.61 | 1.79 | 1.92 |
| B | Control | 0.47 | 1.46 | 2.93 | 1.68 | 1.60 |
| | 110° C. for 120 mins (1) | 0.48 | 1.70 | 3.51 | 1.79 | 1.87 |
| | 110° C. for 120 mins (2) | 0.50 | 1.70 | 3.50 | 1.77 | 1.87 |
| | 121° C. for 20 mins (1) | 0.51 | 1.71 | 3.54 | 1.77 | 1.89 |
| | 121° C. for 20 mins (2) | 0.49 | 1.73 | 3.60 | 1.80 | 1.91 |
| | 121° C. for 30 mins (1) | 0.50 | 1.75 | 3.59 | 1.77 | 1.92 |
| | 121° C. for 30 mins (2) | 0.48 | 1.76 | 3.71 | 1.84 | 1.94 |
| C | Control | 0.48 | 1.48 | 2.98 | 1.69 | 1.62 |
| | 121° C. for 20 mins (1) | 0.51 | 1.78 | 3.73 | 1.81 | 1.97 |
| | 121° C. for 20 mins (2) | 0.51 | 1.79 | 3.74 | 1.81 | 1.97 |
| D | Control | 0.48 | 1.51 | 3.06 | 1.71 | 1.66 |
| | 121° C. 20 mins (1) | 0.51 | 1.78 | 3.69 | 1.79 | 1.96 |

TABLE 6-continued

Particle Size Distribution Results for Heated Budesonide Concentrates

| Concentrate | Heating Regime | Average Values in μm | | | | |
|---|---|---|---|---|---|---|
| | | Dv10* | Dv50* | Dv90* | SPAN** | D[4, 3]† |
| | 121° C. 20 mins (2) | 0.51 | 1.76 | 3.66 | 1.79 | 1.94 |

*Dv = Volume Diameter at $10^{th}$, $50^{th}$ or $90^{th}$ percentile of the distribution
**Span = (Dv90 − Dv10)/Dv90
†Volume Moment Mean Diameter

Example 2

Heat Sterilization of Budesonide

Study 2

The apparent concentration dependent reduction of degradation product production observed in Example 1 prompted a subsequent study to determine the lowest budesonide concentration limits that could be sterilized while maintaining acceptable degradation and particle sizes. The samples were prepared according to the procedures outlined in Example 1, with the exception that the heating and time exposures were limited to 121° C. for 30 minutes.

Table 7 describes a budesonide concentrate from which subsequent dilutions were made. The heated and diluted samples were analyzed to determine budesonide content and impurity levels (both known and unknown), the results of which are presented in Tables 8, with particle size distribution reported in Table 9. FIGS. 3 and 4 graphically display respectively the budesonide content and total impurities of the heat stressed diluted samples. Sterilization was confirmed by use of bioindicators that were heated concomitantly with the sample concentrates.

The data from this study tends to confirm previous observations indicating that the lower the corticosteroid concentration to be heat sterilized, the greater the associated degradation products. It would appear, based on both total degradants produced and resulting particle sizes that the lowest concentration for producing an acceptable heat sterilized product is about 15 mg/ml (see FIGS. 3 & 4).

TABLE 7

Formulation of Budesonide Concentrate and Diluent

| | | Concentration (mg/ml) |
|---|---|---|
| Budesonide | Concentrate | 37.5 |
| | Diluent | 0 |
| Polysorbate 80 Ph. Eur. | Concentrate | 30 |
| | Diluent | 0 |
| Sodium Chloride Ph. Eur. | All | 8.5 |
| Sodium Citrate Dihydrate Ph. Eur. | All | 0.5 |
| Citric Acid Monohydrate Ph. Eur. | All | 0.31 |
| Disodium Edetate Dihydrate Ph. Eur. | All | 0.1 |

TABLE 8

Related Substances Results for Budesonide Concentrates in Budesonide

| | Concentrate Sample | | | | | | | |
|---|---|---|---|---|---|---|---|---|
| Impurity | 0.5 mg/ml of Active | | 1 mg/ml of Active | | 2 mg/ml of Active | | 3 mg/ml of Active | |
| (% w.r.t. active) | Control | Heated | Control | Heated | Control | Heated | Control | Heated |
| 16α Hydropredisolone | ND | 0.11 | N.D. | 0.03 | N.D. | N.D. | N.D. | N.D. |
| Desonide | ND | 0.06 | N.D. | 0.03 | N.D. | N.D. | N.D. | N.D. |
| 21-Dehydro-budesonide | ND | ND | NT. | N.T. | N.T. | N.T. | N.T. | N.T. |
| Budesonide-1,2-dihydro | ND | 0.95 | N.D. | 0.28 | N.D. | 0.20 | N.D. | 0.05 |
| 22-Methyl-Homologue of Budesonide | ND | ND | N.D. | N.D. | ND. | N.D. | N.D. | N.D. |
| D-homobudesonide | ND | 0.02 | N.D. | N.D. | ND. | N.D. | N.D. | N.D. |
| 14,15-dehydrobudesonide | ND | ND | N.D. | N.D. | N.D. | N.D. | N.D. | N.D. |
| S-11-keto budesonide | 0.02 | 0.33 | 0.02 | 0.35 | 0.02 | 0.16 | 0.02 | 0.15 |
| R-11-keto budesonide | 0.02 | 0.15 | 0.02 | 0.13 | 0.02 | 0.08 | 0.02 | 0.07 |
| S-21-acetate budesonide | ND | ND | N.D. | N.D. | N.D. | N.D. | N.D. | N.D. |
| R-21-acetate budesonide | ND | ND | N.D. | N.D. | N.D. | N.D. | N.D. | N.D. |
| Total Known | 0.00 | 1.60 | 0.00 | 0.76 | 0.00 | 0.44 | 0.00 | 0.27 |
| Max Unknown | 0.00 | 0.48 | 0.00 | 0.14 | 0.00 | 0.07 | 0.00 | 0.07 |
| Total Unknown | 0.00 | 1.38 | 0.00 | 0.42 | 0.00 | 0.13 | 0.00 | 0.07 |

TABLE 8-continued

Related Substances Results for Budesonide Concentrates in Budesonide

| | | | | | | | | |
|---|---|---|---|---|---|---|---|---|
| Total Impurities | 0.00 | 2.98 | 0.00 | 1.18 | 0.00 | 0.57 | 0.00 | 0.34 |

| | Concentrate Sample | | | | | | | |
|---|---|---|---|---|---|---|---|---|
| | 4 mg/ml of Active | | 5 mg/ml of Active | | 10 mg/ml of Active | | 15 mg/ml of Active | |
| Impurity (% w.r.t. active) | Control | Heated | Control | Heated | Control | Heated | Control | Heated |
| 16α Hydropredisolone | N.D. | N.D. | ND | ND | ND | ND | ND | ND |
| Desonide | N.D. | N.D. | ND | ND | ND | ND | ND | ND |
| 21-Dehydro-budesonide | N.T. | N.T. | ND | ND | ND | ND | ND | ND |
| Budesonide-1,2-dihydro | N.D. | 0.13 | ND | ND | ND | ND | ND | ND |
| 22-Methyl-Homologue of Budesonide | N.D. | N.D. | ND | ND | ND | ND | ND | ND |
| D-homobudesonide | N.D. | N.D. | ND | ND | ND | ND | ND | ND |
| 14,15-dehydrobudesonide | N.D. | N.D. | ND | ND | ND | ND | ND | ND |
| S-11-keto budesonide | 0.02 | 0.10 | 0.02 | 0.09 | 0.02 | 0.04 | 0.02 | 0.04 |
| R-11-keto budesonide | 0.02 | 0.05 | 0.02 | 0.05 | 0.02 | 0.03 | 0.02 | 0.03 |
| S-21-acetate budesonide | N.D. | 0.04 | ND | ND | ND | ND | ND | ND |
| R-21-acetate budesonide | N.D. | N.D. | ND | ND | ND | ND | ND | ND |
| Total Known | 0.00 | 0.28 | 0.00 | 0.14 | 0.00 | 0.00 | 0.00 | 0.00 |
| Max Unknown | 0.00 | 0.06 | 0.00 | 0.06 | 0.00 | 0.09 | 0.06 | 0.08 |
| Total Unknown | 0.00 | 0.06 | 0.00 | 0.06 | 0.00 | 0.09 | 0.06 | 0.08 |
| Total Impurities | 0.00 | 0.34 | 0.00 | 0.20 | 0.00 | 0.09 | 0.06 | 0.08 |

| | Concentrate Sample | | | | | | | |
|---|---|---|---|---|---|---|---|---|
| | 20 mg/ml of Active | | 25 mg/ml of Active | | 30 mg/ml of Active | | 35 mg/ml of Active | |
| Impurity (% w.r.t. active) | Control | Heated | Control | Heated | Control | Heated | Control | Heated |
| 16α Hydropredisolone | ND | ND | ND | ND | ND | ND | ND | ND |
| Desonide | ND | ND | ND | ND | ND | ND | ND | ND |
| 21-Dehydro-budesonide | ND | ND | ND | ND | ND | ND | ND | ND |
| Budesonide-1,2-dihydro | ND | ND | ND | ND | ND | ND | ND | ND |
| 22-Methyl-Homologue of Budesonide | ND | ND | ND | ND | ND | ND | ND | ND |
| D-homobudesonide | ND | ND | ND | ND | ND | ND | ND | ND |
| 14,15 dehydrobudesonide | ND | ND | ND | ND | 0.01 | ND | ND | 0.01 |
| S-11-keto budesonide | 0.02 | 0.04 | 0.02 | 0.03 | 0.02 | 0.03 | 0.02 | 0.02 |
| R-11-keto budesonide | 0.02 | 0.03 | 0.02 | 0.02 | 0.02 | 0.02 | 0.02 | 0.02 |
| S-21-acetate budesonide | ND | ND | ND | ND | ND | ND | ND | ND |
| R-21-acetate budesonide | ND | ND | ND | ND | ND | ND | ND | ND |
| Total Known | 0.00 | 0.00 | 0.00 | 0.00 | 0.00 | 0.00 | 0.00 | 0.00 |
| Max Unknown | 0.07 | 0.10 | 0.08 | 0.09 | 0.00 | 0.10 | 0.09 | 0.10 |
| Total Unknown | 0.07 | 0.10 | 0.08 | 0.09 | 0.00 | 0.10 | 0.09 | 0.10 |
| Total Impurities | 0.07 | 0.10 | 0.08 | 0.09 | 0.00 | 0.10 | 0.09 | 0.10 |

ND—not detectable (i.e. below the limit of detection)
NT—not tested

TABLE 9

Particle Size Distribution Results for Budesonide Concentrates in Budesonide

| Concentrate (mg/ml of Active) | Heating Regime | Values in μm | | | | |
|---|---|---|---|---|---|---|
| | | Dv10 | Dv50 | Dv90 | SPAN | D[4,3] |
| 0.5 | Control | 0.56 | 2.10 | 4.75 | 2.00 | 2.43 |
| | Heated | a | a | a | a | a |
| | Heated | NT | NT | NT | NT | NT |
| 5[b] | Control | 0.73 | 2.26 | 4.76 | 1.78 | 2.53 |
| | Heated | 0.60 | 3.09 | 6.92 | 2.05 | 3.97 |
| 10[b] | Control | 0.72 | 2.23 | 4.71 | 1.79 | 2.51 |
| | Heated | 0.66 | 2.97 | 6.37 | 1.92 | 3.51 |
| 15 | Control | 0.70 | 2.21 | 4.67 | 1.80 | 2.49 |
| | Heated | 0.66 | 2.94 | 6.08 | 1.85 | 3.21 |
| 25 | Control | 0.71 | 2.22 | 4.69 | 1.79 | 2.50 |
| | Heated | 0.68 | 2.88 | 5.94 | 1.83 | 3.15 |
| 35 | Control | 0.68 | 2.93 | 6.01 | 1.82 | 3.19 |
| | Heated | 0.67 | 2.89 | 5.96 | 1.83 | 3.16 | a - The particle size distribution of the samples was unable to be obtained by laser light scattering due to insufficient suspended particles after heating.
[b] A small percentage of particles of greater than 40 μm were detected.
NT—not tested Example 3

Heat Sterilization of Beclomethasone Dipropionate

The procedures of Example 1% were used to prepare beclomethasone concentrates and dilutions as indicated in Table 10. Determination of impurity levels and particle size were also determined as outlined above. The results indicate (data not shown) that there was no significant change in beclomethasone content or increase in impurities upon heating in the autoclave. Additionally, autoclaving resulted in no significant change in particle size distribution.

TABLE 10

Formulations of BDP Concentrate and BDP Product Suspension Heat regimen 121/30

| | | Concentration (mg/ml) |
|---|---|---|
| BDP | Concentrate | 75 |
| | Product Suspension | 0.5 |
| Polysorbate 80 Ph. Eur. | Concentrate | 30 |
| | Product Suspension | 0.2 |
| Sodium Chloride Ph. Eur. | All | 8.5 |
| Sodium Citrate Dihydrate Ph. Eur. | All | 0.5 |
| Citric Acid Monohydrate Ph. Eur. | All | 0.31 |
| Disodium Edetate Dihydrate Ph. Eur. | All | 0.1 |

EQUIVALENTS

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claim is:

1. A method for the sterilization of a labile glucocorticosteroid, comprising the step of applying moist heat to an aqueous suspension of a labile glucocorticosteroid for a sterilizing-effective time, wherein at least 70% of the glucocorticosteroid is in the form of a suspension during heating and at least one surfactant is present in the aqueous suspension during heating.

2. A method for the sterilization of a glucocorticosteroid, comprising the step of heating an aqueous suspension of a glucocorticosteroid, wherein the glucocorticosteroid has a sufficiently low solubility in water and is used in a sufficient amount that at least 70% of the glucocorticosteroid is in the form of a suspension during heating and wherein at least one surfactant is present in the aqueous suspension during heating.

3. The method of claim 2, wherein said heating is at a temperature of from about 101° C. to about 145° C.

4. The method of claim 2, wherein said heating is carried out by autoclaving.

5. The method of claim 2, wherein said heating is carried out for about 2 to about 180 minutes.

6. The method of claim 1, wherein the surfactant is present during heating at a concentration of from about 0.75 mg/ml to about 60 mg/ml.

7. The method of claim 2, wherein the glucocorticosteroid is budesonide or beclomethasone dipropionate.

8. The method of claim 6, wherein said glucocorticosteroid is budesonide, and the heating is carried out at 121° C. for about 20-30 minutes or at 110° C. for about 120 minutes.

9. The method of claim 6, wherein said glucocorticosteroid is beclomethasone dipropionate, and the heating carried out at 121° C. for about 20-30 minutes or at 110° C. for about 120 minutes.

10. A method for the sterilization of budesonide, comprising the step of heating an aqueous suspension of budesonide at a concentration of from about 15 mg/ml to about 150 mg/ml at a temperature of from about 101° C. to about 145° C. for about 2 to about 180 minutes, wherein at least 70% of the budesonide is in the form of a suspension during heating and at least one surfactant is present in the aqueous suspension during heating.

11. The method of claim 10, further comprising the step of diluting the aqueous suspension to a pharmaceutically suitable concentration.

* * * * *